(12) United States Patent
Dorn et al.

(10) Patent No.: US 11,069,428 B2
(45) Date of Patent: Jul. 20, 2021

(54) EVALUATION METHOD FOR MEDICAL DATA

(71) Applicants: Karlheinz Dorn, Kalchreuth (DE); Thomas Goßler, Erlangen (DE); Andrew John Hewett, Erlangen (DE); Vladyslav Ukis, Nürnberg (UA)

(72) Inventors: Karlheinz Dorn, Kalchreuth (DE); Thomas Goßler, Erlangen (DE); Andrew John Hewett, Erlangen (DE); Vladyslav Ukis, Nürnberg (UA)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1232 days.

(21) Appl. No.: 14/933,753

(22) Filed: Nov. 5, 2015

(65) Prior Publication Data

US 2016/0125138 A1     May 5, 2016

(30) Foreign Application Priority Data

Nov. 5, 2014    (EP) .................................. 14191809

(51) Int. Cl.
*G16H 10/60*     (2018.01)
*G06F 21/62*     (2013.01)
(Continued)

(52) U.S. Cl.
CPC ........... *G16H 10/60* (2018.01); *G06F 16/245* (2019.01); *G06F 21/6254* (2013.01); *G16H 30/20* (2018.01); *G16H 50/70* (2018.01)

(58) Field of Classification Search
None
See application file for complete search history.

(56) References Cited

U.S. PATENT DOCUMENTS

2008/0103834 A1 * 5/2008 Reiner ................... A61B 6/542
                                                                 705/3
2008/0243539 A1 * 10/2008 Barish .................. G06F 19/321
                                                                 705/2
(Continued)

FOREIGN PATENT DOCUMENTS

EP          2 645 330 B1 * 3/2012      ............... A61B 5/00

OTHER PUBLICATIONS

Muehlbeock, TheHiveDB image data management and analsys framework, Technology Report Article (Year: 2014).*
(Continued)

*Primary Examiner* — Rachelle L Reichert
(74) *Attorney, Agent, or Firm* — Lempia Summerfield Katz LLC

(57) ABSTRACT

Measurement results are acquired by a number of medical imaging systems in each case using a respective measurement protocol and by applying a respective dose. Data records are automatically placed in a cloud by the systems or a PACS connected to the respective system. Measurement protocols, applied doses, and anonymized images of the data records are referenced among each other. The data records placed in the cloud are assigned the respective examination type and an identification of the respective system and/or an identification of the type of respective system. The cloud accepts data queries from users. The data queries as a search criterion specify at least the examination type, the identification of the respective system, and/or the identification of the type of the respective system. The data records are determined by the cloud in accordance with the respective data query and are made available to the respective user.

20 Claims, 2 Drawing Sheets

(51) Int. Cl.
    *G06F 16/245*     (2019.01)
    *G16H 50/70*     (2018.01)
    *G16H 30/20*     (2018.01)

(56) References Cited

U.S. PATENT DOCUMENTS

| | | | |
|---|---|---|---|
| 2011/0110568 A1* | 5/2011 | Vesper | G06F 19/321 |
| | | | 382/128 |
| 2013/0159019 A1* | 6/2013 | Reicher | G16H 15/00 |
| | | | 705/3 |
| 2014/0142984 A1 | 5/2014 | Wright et al. | |
| 2014/0188513 A1 | 7/2014 | Balignasay et al. | |
| 2015/0100572 A1* | 4/2015 | Kalafut | G06Q 50/24 |
| | | | 707/736 |

OTHER PUBLICATIONS

European Search Report for related EP Application No. 14191809.4, dated May 11, 2015, with English Translation.

\* cited by examiner

EVALUATION METHOD FOR MEDICAL DATA

This application claims the benefit of EP14191809.4, filed on Nov. 5, 2014, which is hereby incorporated by reference in its entirety.

BACKGROUND

The present embodiments relate to an evaluation method for medical data.

In hospitals and other medical facilities, a plurality of medical imaging systems is operated. Operation is performed by users. Users often have just limited knowledge about the possibilities and qualities of the medical imaging systems. The users therefore operate the medical imaging systems generally according to the specifications of the manufacturer of the respective medical imaging system. In many cases, on account of experience with operating the respective medical imaging system, users develop a feeling as to when and to what extent the users may deviate from the specifications of the manufacturer. This nevertheless generally requires considerable experience. Users generally lack any possibility of being able to estimate or classify the quality and/or the optimal nature of the respective mode of operation of the respective medical imaging system.

During operation of the medical imaging systems, a plurality of patient data moreover accumulates. For example, the images acquired by the medical imaging systems accumulate. These images may in principle, provided the images are anonymized, be used as teaching and comparison material. However, the number of images accumulating in individual hospitals is often too small to form the basis here.

SUMMARY AND DESCRIPTION

The scope of the present invention is defined solely by the appended claims and is not affected to any degree by the statements within this summary.

The present embodiments may obviate one or more of the drawbacks or limitations in the related art. For example, possibilities for the user, using a uniform database, both to be able to estimate and classify the mode of operation of the medical imaging system operated thereby in each case are created, and case studies and suchlike may also be performed.

In one or more of the present embodiments, an evaluation method is created for medical data. Measurement results are acquired by a number of medical imaging systems in each case using a respective measurement protocol and by applying a respective dose. Data records are automatically placed in each case in a cloud by the medical imaging systems or a PACS connected to the respective medical imaging system. The data records include at least the respective measurement protocol used, the respective applied dose, and in anonymized form, images derived in each case from the acquired measurement results. The measurement protocols, the applied doses, and the anonymized images of the respective data record are referenced among one another. The respective examination type and an identification of the respective medical imaging system and/or an identification of the type of respective medical imaging system are assigned to the data records placed in the cloud. The cloud accepts respective data queries from users. The data queries, as a search criterion, at least specify the examination type and/or the identification of the respective medical imaging system and/or the identification of the type of respective medical imaging system. The data records placed in the cloud are determined by the cloud according to the respective data query and made available to the respective user. The users additionally specify in data queries whether the respective measurement protocol used, the respective applied dose, and/or in anonymized form, the respective images are to be made available. The possibility is offered to the users of the cloud, based on the data records made available, to retrieve additional contents of these data records.

In one embodiment, the data records may exclusively contain the afore-cited data. Alternatively, the data records automatically placed in the cloud by the medical imaging systems or the PACS connected to the respective medical imaging system may also include data derived from the images in anonymized form. This data may, for example, be free text and/or a subjective qualitative assessment or classification of the images by the operator. This data is also linked to the remaining data of the respective data record.

It is similarly possible for the data records placed automatically in the cloud by the medical imaging systems or the PACS connected to the respective medical imaging system to include, alternatively or in addition to the additional data, additional data of the image acquisition. This data may be, for example, parameters of the image acquisition or characteristics of the respective medical imaging system. This data is also linked to the remaining data of the respective data record.

Non-anonymized image data may also be placed in the cloud by the medical imaging systems or the PACS connected to the respective medical imaging system. This data is, however, placed in the cloud in a form that is protected from unauthorized access. This data (e.g., the non-anonymized image data) may be placed in the cloud as independent data records, but nevertheless has a reference to the measurement protocol used and the data record containing the applied dose. As a result, based on the non-anonymized image data, the data record containing the measurement protocol used and the applied dose may be located. By contrast, based on the data record containing the measurement protocol used and the applied dose, the non-anonymized image data may not be located.

The medical imaging systems may be embodied, as required. For example, the medical imaging systems may be embodied in each case as an x-ray system, a CT scanner, a C-arm system, or as another medical imaging system.

BRIEF DESCRIPTION OF THE DRAWINGS

The above-described characteristics, features and advantages of the present embodiments, as well as the manner in which these are achieved, will become more clearly and easily intelligible in connection with the following description of the exemplary embodiments, which are explained in more detail in conjunction with the drawings, in which.

DETAILED DESCRIPTION

Figure 1:
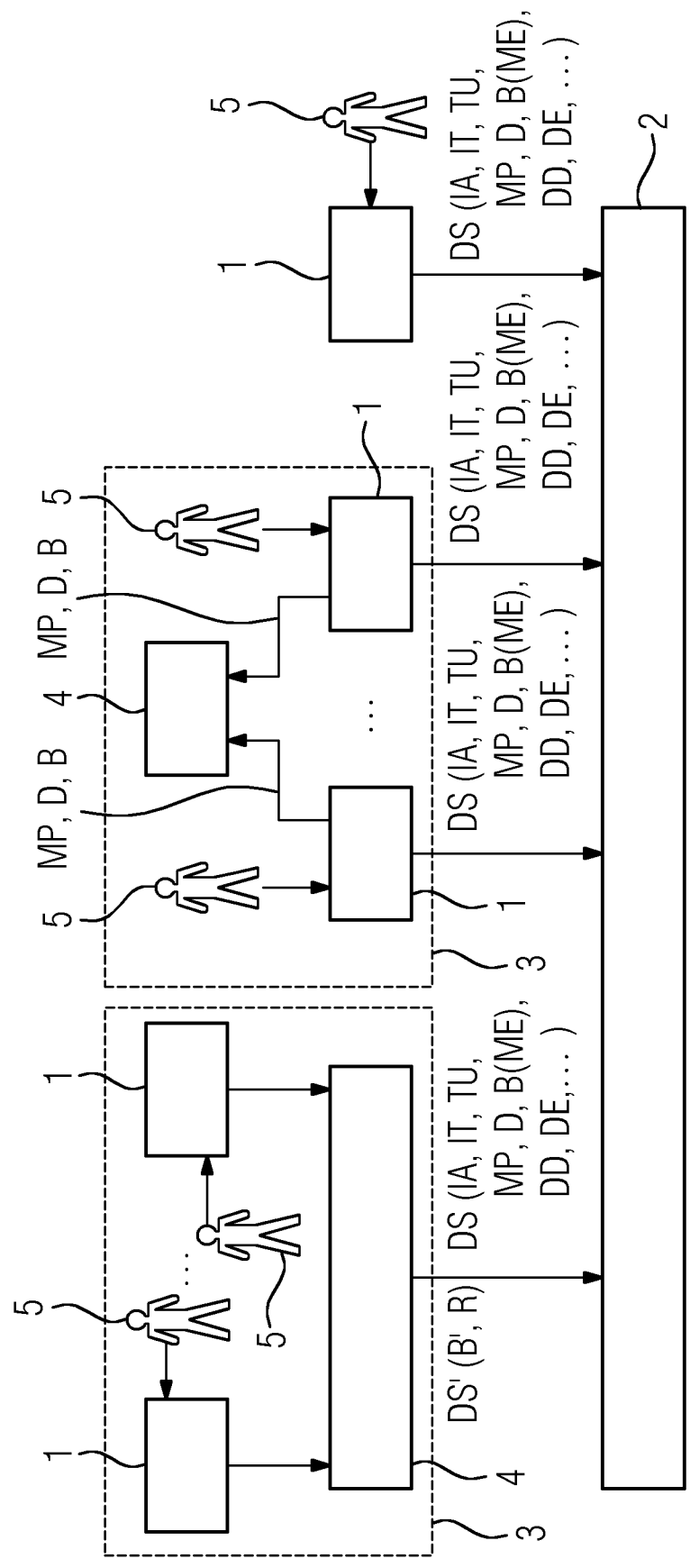
FIG. 1 shows one embodiment of a networked system.

According to FIG. 1, a number of medical imaging systems 1 are connected to a cloud 2 (e.g., a cloud database). The medical imaging systems 1 may be embodied, for example, in each case as an x-ray system, a CT scanner, or as a C-arm system. Alternatively, the medical imaging systems 1 may be embodied as other medical imaging systems (e.g., as a magnetic resonance system). The medical imaging systems 1 may be distributed all over the world. For example, the medical imaging systems 1 may be arranged within hospitals 3, and within the respective hospital 3, the medical imaging system 1 may be connected to a respective picture archiving and communication system (PACS) 4.

Based on specifications by an operator 5, the medical imaging systems 1 are operated using a respective measurement protocol MP. During the use of the respective measurement protocol MP, the respective medical imaging system 1 applies a respective dose D of radiation to a patient (not shown) (e.g., in the case of a magnetic resonance system of magnetic radiation or in the case of an x-ray system, a CT scanner or a C-arm system of ionizing radiation). On account of the measurement protocol MP, measurement results ME are acquired by the respective medical imaging system 1. The measurement results ME may already themselves be direct images B. Alternatively, images B may be derived from the acquired measurement results ME. The images B and the measurement protocols MP used to acquire the measurement results ME are supplied by the respective medical imaging system 1, if available, to the respective PACS 4. Data records DS are then automatically placed in the cloud 2 by the respective PACS 4. The data records DS include (see also FIG. 2) at least the respective measurement protocol used MP, the respective applied dose D, and the images B. The images B are however anonymized prior to placement in the cloud 2. Alternatively, the automatic placement of the data records DS may also take place using the respective medical imaging system 1. This applies irrespective of whether or not the respective medical imaging system 1 is connected to a PACS 4.

Within the respective data record DS, the respective measurement protocol MP, the applied dose D, and the anonymized images B are referenced among one another. It is therefore possible, based on the respective measurement protocol MP, to locate the applied dose D and the anonymized images B of the corresponding data record DS. It is similarly possible, based on the respective applied dose D, to locate the respective measurement protocol MP and the anonymized images B of the corresponding data record DS. It is similarly possible, based on the anonymized images B, to locate the measurement protocol MP and the applied dose D of the corresponding data record DS.

The data records DS may further be assigned data DD in anonymized form from the respective medical imaging system 1 or from the PACS 4 connected to the respective medical imaging system 1. The data is derived from the images B. The data DD is also linked to the remaining data of the respective data record DS. The data DD may be, for example, free text or a subjective qualitative classification of the images B. The free text or the classification is in such a case predetermined to the respective medical imaging system 1 or the corresponding PACS 4 by the respective user 5. Placing the data DD in the cloud 2 and linking the same with the remaining data MP, D, B of the respective data record DS only takes place automatically.

Additional data DE of the image acquisition may be assigned to the data records DS. The data DE is also linked to the remaining data of the respective data record DS. The data may be, for example, parameters of the image acquisition or characteristics of the respective medical imaging system 1. The assignment of the data DE and its link with the remaining data of the respective data record DS may be performed if necessary by the respective medical imaging system 1 or by the PACS 4 connected to the respective medical imaging system 1. In one embodiment, the assignment of the data DE and its link with the remaining data MP, D, B, and possibly DD of the respective data record DS may be performed within the cloud 2.

In addition to the afore-cited data MP, D, B and if necessary DD and/or DE, the respective examination type TU is additionally assigned to the respective data record DS (e.g., whether this is an examination of the chest, a foot, a hand, an upper arm etc. of the patient). This assignment takes place by the respective medical imaging system 1. An identification IA of the respective medical imaging system 1 is also assigned additionally to the respective data record DS. This assignment also takes place by the respective medical imaging system 1. Alternatively or in addition to assigning the identification IA, an identification IT of the type of the respective medical imaging system 1 may be assigned to the respective data record DS. If the assignment takes place as an alternative to assigning the identification IA, this assignment is also performed by the respective medical imaging system 1. If the assignment takes place in addition to assigning the identification IA, this assignment may alternatively be performed by the respective medical imaging system 1, the associated PACS 4, or by the cloud 2.

Figure 2:
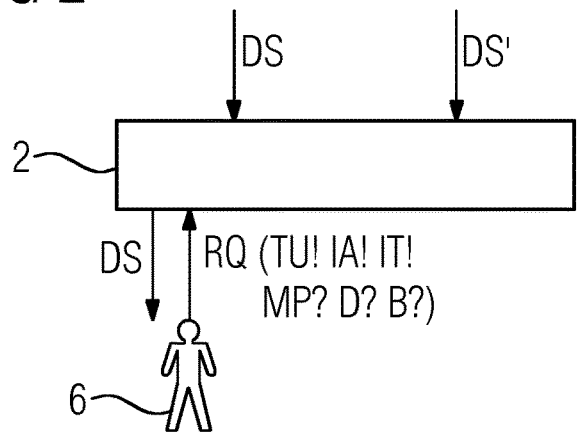
FIG. 2 shows an exemplary communication with a cloud.
Figure 3:
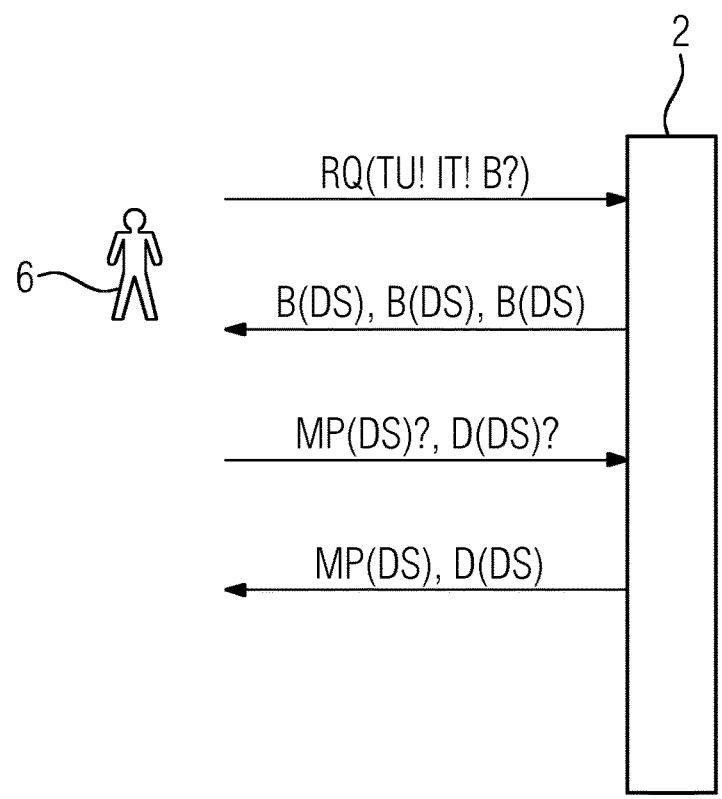
FIG. 3 shows an exemplary course of a communication with the cloud.

According to FIGS. 2 and 3, the cloud 2 accepts respective data queries RQ from users 6. This may alternatively be operators 5 or persons who differ from the operators 5. The data queries RQ specify as a search criterion at least the examination type TU and/or the identification IA of the respective medical imaging system 1 and/or the identification IT of the type of the respective medical imaging system 1. This is indicated in FIG. 2 in that the corresponding parameters TU, IA, IT are supplemented with an exclamation mark. It is nevertheless sufficient if only one of these three parameters TU, IA, IT is predetermined in the respective query RQ or only two of these three parameters TU, IA, IT are predetermined.

In one embodiment, further parameters may also be specified as a search criterion (e.g., the measurement protocol MP or the applied dose D). Other parameters may also be specified as a search criterion (e.g., the date upon which a certain data record DS was created or was placed in the cloud 2). Based on the predetermined parameters TU, IA, IT, the data records DS placed in the cloud 2 are determined by the cloud 2 in accordance with the respective data query RQ and are made available to the respective user 6.

In the respective data query RQ, the users 6 also specify which results are to be supplied thereto. The users 6 therefore also specified whether, for example, the respective measurement protocol used MP, the respectively applied dose D, and/or in anonymized form, the respective images B are to be made available. This is indicated in FIG. 2 in that the corresponding parameters MP, D, B are supplemented with an exclamation mark. Provided the examination type TU, the identification IA of the respective medical imaging system 1, and the identification IT of the type of the respective medical imaging system 1 are not already predetermined as a search criterion within the scope of the respective data query RQ, these parameters TU, IA, IT may also be specified as results to be supplied.

Based on the data records DS to be made available (or corresponding queried elements), the possibility is offered to the respective user 6 by the cloud 2 according to FIG. 3 to retrieve additional contents of these data records DS. For example, the respective user 6, once the user 6 has specified, as shown purely by way of example in FIG. 3, firstly only the respective examination type TU as a search criterion and the associated images B of the relevant data records DS as data to be supplied, may select one or a number of the conveyed data records DS and with respect to the selected data records DS retrieve corresponding measurement protocols MP and the associated doses D.

On account of the data records DS placed in the cloud 2, a plurality of evaluations is possible. A few examples are provided below.

If a user 6 would like to find out, for example, how much of a dose D is required for a certain examination as search criterion, the user 6 specifies the examination type TU and the type IT of the medical imaging system 1 available to the user 6. As data to be supplied, the user 6 specifies the images B of the corresponding data records DS. For images B that the user 6 deems to be good or satisfactorily good, the user 6 also queries the measurement protocol used MP and/or the applied dose D. As a result, the user 6 may optimize the operation of the medical imaging system 1 available to the user 6.

If a user 6 would like to know which results are obtained with a certain measurement protocol MP, as the search criterion, the user 6 specifies the examination type TU and the measurement protocol MP. In addition, as the search criterion, the user 6 may specify the type IT of medical imaging system 1 available to the user 6, for example. As data to be supplied, the user 6 in this case specifies the images B. With good images B, the user 6 also queries the applied dose D. As a result, the user 6 may perform an optimization of the operation of the medical imaging system 1 available to the user 6.

If the user 6 would like to perform an estimation of the procedures taken during operation of the medical imaging system 1, as the search criterion, the user 6 specifies the examination type TU and possibly also the type IT of medical imaging system 1 available to the user 6. As data to be supplied, the user 6 specifies the images B and the applied dose D. The user 6 specifies that the data is output with an increasing or decreasing applied dose D.

It is additionally possible in accordance with the representation in FIG. 1 for non-anonymized image data B' to be placed in the cloud 2 by the medical imaging systems 1 or the PACS 4 connected to the respective medical imaging system 1. This placement only then takes place if the placement was authorized beforehand by the respective user 5. The placement takes place in the form in which the image data B' is protected from unauthorized access. For example, the data may be encrypted and/or protected by a password. As a result, sensitive image data B' may be exchanged between different locations and thus different operators 5 and users 6 via the cloud 2.

The non-anonymized image data B' according to FIG. 2 is generally placed in the cloud 2 as independent data records DS'. The independent data records DS' nevertheless generally contain a reference R to the data record DS, which contains the measurement protocol used MP and the applied dose D. Based on the non-anonymized image data B', the data record DS may thus be located, which contains the measurement protocol used MP and the applied dose D. By contrast, based on the data record DS, which contains the measurement protocol used MP and the applied dose D, the non-anonymized image data B' may thus not be located.

In summary, one or more of the present embodiments thus relate to the following situation.

Measurement results ME are acquired by a number of medical imaging systems 1 in each case using a respective measurement protocol MP and by applying a respective dose D. Data records DS are automatically placed in a cloud 2 by the systems 1 or a PACS 4 connected to the respective system 1. The data records include at least the respective measurement protocol used MP, the respective applied dose D, and in anonymized form, images B derived in each case from the acquired measurement results ME. The measurement protocols MP, the applied doses D, and the anonymized images B of the data records DS are referenced among each other. The data records DS placed in the cloud are additionally assigned to the respective examination type TU and an identification IA of the respective system 1 and/or an identification IT of the type of the respective system 1. The cloud 2 accepts data queries RQ from users 6, which as a search criterion, specify at least the examination type TU, the identification IA of the respective system 1, and/or the identification IT of the type of the respective system 1. The data records DS are determined by the cloud 2 in accordance with the respective data query RQ and are made available to the respective user 6. The users 6 specify in corresponding data queries RQ additionally which data is to be made available. Users 6 are offered the possibility by the cloud 2, based on the data records DS made available, to retrieve additional contents of these data records DS.

The present embodiments have many advantages. A comprehensive uniform database, for example, that may be evaluated as standard worldwide is created. An individualized exchange of confidential patient data may also be provided. On account of the automated placement of the data records DS, the cloud 2 is automatically continuously expanded, the database in other words widened.

Although the invention has been illustrated and described in greater detail with reference to the exemplary embodiments, the invention is not limited by the examples disclosed. The person skilled in the art will be able to derive other variations on this basis without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An evaluation method for medical data, the evaluation method comprising:

acquiring, by a number of medical imaging systems, measurement results using a respective measurement protocol and by applying a respective dose, wherein the respective measurement protocol is used to operate a respective medical imaging system; and automatically placing, in each case, data records in a cloud by the medical imaging systems or a PACS connected to the respective medical imaging system, the data records including at least the respective measurement protocol used, the respective applied dose, and in anonymized form, images derived in each case from the acquired measurement results, wherein the measurement protocols, the applied doses, and the anonymized images of respective data records are referenced among one another as linked data items, such that locating one of the linked data items allows the other linked data items to be located, wherein a respective examination type and an identification of the respective medical imaging system, an identification of the type of respective medical imaging system, or a combination thereof are assigned to the data records placed in the cloud, the respective examination type indicative of a specific region of an object being measured by the respective medical imaging system, wherein the cloud accepts respective data queries from respective users, wherein the respective data queries as a search criterion at least specify the examination type and the identification of the respective medical imaging system, the identification of the type of the respective medical imaging system, or any combination thereof, wherein the cloud identifies a subset of the data records placed in the cloud according to each of the respective data queries and makes available the subset of the data records to the respective users, and wherein the respective users additionally specify in the respective data queries a type of data to be supplied to the respective users as respective results of the respective data queries, the type of data being the respective measurement protocol used, the respective applied dose, the respective anonymized images, or any combination thereof.

2. The evaluation method of claim 1, wherein the data records placed automatically in the cloud by the medical imaging systems or the PACS connected to the respective medical imaging system also comprise data derived from the images in anonymized form, and wherein the data is also linked to remaining data of the respective data records.

3. The evaluation method of claim 1, wherein the data records placed automatically in the cloud by the medical imaging systems or the PACS connected to the respective medical imaging system comprise additional data of the image acquisition, and wherein the data is also linked to remaining data of the respective data records.

4. The evaluation method of claim 1, further comprising placing non-anonymized image data in the cloud in a form that is protected from unauthorized access by the medical imaging systems or the PACS connected to the respective medical imaging system.

5. The evaluation method of claim 4, wherein the non-anonymized image data is placed in the cloud as independent data records but has a reference to the data record containing the measurement protocol used and the applied dose.

6. The evaluation method of claim 1, wherein the medical imaging systems comprise an x-ray system, a CT-scanner, a C-arm system, another medical imaging system, or any combination thereof.

7. The evaluation method of claim 2, wherein the data records placed automatically in the cloud by the medical imaging systems or the PACS connected to the respective medical imaging system comprise additional data of the image acquisition, and
wherein the data is also linked to the remaining data of the respective data records.

8. The evaluation method of claim 2, further comprising placing non-anonymized image data in the cloud in a form that is protected from unauthorized access by the medical imaging systems or the PACS connected to the respective medical imaging system.

9. The evaluation method of claim 3, further comprising placing non-anonymized image data in the cloud in a form that is protected from unauthorized access by the medical imaging systems or the PACS connected to the respective medical imaging system.

10. The evaluation method of claim 2, wherein the medical imaging systems comprise an x-ray system, a CT-scanner, a C-arm system, another medical imaging system, or any combination thereof.

11. The evaluation method of claim 3, wherein the medical imaging systems comprise an x-ray system, a CT-scanner, a C-arm system, another medical imaging system, or any combination thereof.

12. The evaluation method of claim 4, wherein the medical imaging systems comprise an x-ray system, a CT-scanner, a C-arm system, another medical imaging system, or any combination thereof.

13. The evaluation method of claim 5, wherein the medical imaging systems comprise an x-ray system, a CT-scanner, a C-arm system, another medical imaging system, or any combination thereof.

14. The evaluation method of claim 1, wherein the respective examination type and the identification of the respective medical imaging system are assigned to the data records placed in the cloud, and wherein the respective data queries as a search criterion at least specify the examination type and the identification of the respective medical imaging system.

15. The evaluation method of claim 1, wherein a possibility is offered to the respective users of the cloud, based on the data records made available to the respective users, to retrieve additional contents of the data records.

16. An evaluation method for medical data, the evaluation method comprising:

acquiring, by a number of medical imaging systems, measurement results using a respective measurement protocol and by applying a respective dose; and automatically placing, in each case, data records in a cloud database by the medical imaging systems or a PACS connected to the respective medical imaging system, the data records including at least the respective measurement protocol used, the respective applied dose, and in anonymized form, images derived in each case from the acquired measurement results, wherein the measurement protocols, the applied doses, and the anonymized images of respective data records are referenced among one another, wherein a respective examination type and an identification of the respective medical imaging system, an identification of the type of respective medical imaging system, or a combination thereof are assigned to the data records placed in the cloud database, the respective examination type indicative of a specific region of an object being measured by the respective medical imaging system, wherein the cloud database accepts respective data queries from respective users, wherein the respective data queries as a search criterion at least specify the examination type and the identification of the respective medical imaging system, the identification of the type of the respective medical imaging system, or any combination thereof, wherein the cloud database determines a subset of the data records placed in the cloud database according to each of the respective data queries and makes available the subset of the data records to the respective users, and wherein the respective users additionally specify in the respective data queries a type of data to be supplied to the respective users as respective results of the respective data queries, the type of data being the respective measurement protocol used, the respective applied dose, the respective anonymized images, or any combination thereof.

17. The evaluation method of claim 16, wherein a possibility is offered to the respective users of the cloud database, based on the data records made available to the respective users, to retrieve additional contents of the data records.

18. An evaluation method for medical data, the evaluation method comprising:

acquiring, by a number of medical imaging systems, measurement results using a respective measurement protocol and by applying a respective dose; and automatically placing, in each case, data records in a cloud by the medical imaging systems or a PACS connected to the respective medical imaging system, the data records including at least the respective measurement protocol used and the respective applied dose, wherein the measurement protocols and the applied doses are referenced among one another, wherein a respective examination type and an identification of the respective medical imaging system, an identification of the type of respective medical imaging system, or a combination thereof are assigned to the data records placed in the cloud, wherein the cloud accepts respective data queries from respective users, wherein the respective data queries as a search criterion at least specify the examination type and the identification of the respective medical imaging system, the identification of the type of the respective medical imaging system, or any combination thereof, wherein the cloud identifies a subset of the data records placed in the cloud according to each of the respective data queries and makes available the subset of the data records to the respective users, and wherein the respective users additionally specify in the respective data queries a type of data to be supplied to the respective users as respective results of the respective data queries, the type of data being the respective measurement protocol used, the respective applied dose, or any combination thereof.

19. The evaluation method of claim 18, wherein the data records further include, in anonymized form, images derived in each case from the acquired measurement results, and wherein the measurement protocols, the applied doses, and the anonymized images of the respective data records are referenced among one another.

20. The evaluation method of claim 18, wherein a possibility is offered to the respective users of the cloud, based on the data records made available to the respective users, to retrieve additional contents of the data records.

* * * * *